United States Patent [19]

Liss et al.

[11] Patent Number: 4,833,090

[45] Date of Patent: May 23, 1989

[54] PRESERVATION OF GLUCOSE IN BLOOD

[76] Inventors: Eberhard Liss; Inge Liss, both of Schütte-Lanz-Str. 94a, Berlin, Fed. Rep. of Germany

[21] Appl. No.: 165,454

[22] PCT Filed: Aug. 6, 1986

[86] PCT No.: PCT/DE86/00320

§ 371 Date: Mar. 30, 1987

§ 102(e) Date: Mar. 30, 1987

[87] PCT Pub. No.: WO87/00769

PCT Pub. Date: Feb. 12, 1987

Related U.S. Application Data

[63] Continuation of Ser. No. 37,357, Mar. 30, 1987, abandoned.

[30] Foreign Application Priority Data

Aug. 8, 1985 [DE] Fed. Rep. of Germany ....... 3528730
Aug. 9, 1985 [DE] Fed. Rep. of Germany ....... 3532477
Nov. 7, 1985 [DE] Fed. Rep. of Germany ....... 3539784

[51] Int. Cl.$^4$ ............................................ G01N 33/48
[52] U.S. Cl. .......................................... 436/14; 435/2; 436/15; 436/16; 436/18
[58] Field of Search .................... 436/95, 14, 174–176, 436/63; 435/14

[56] References Cited

U.S. PATENT DOCUMENTS 3,925,153 12/1975 Caborit .................................. 435/2
4,049,795 9/1977 Laborit ................................ 514/921
4,054,488 10/1977 Marbach ................................ 435/2
4,438,199 3/1984 Miwa et al. ....................... 435/14 X

OTHER PUBLICATIONS

Clinical Chemistry, vol. 26, No. 8, pp. 1228–1229/Jul. 1980.
Chemical Abstracts, vol. 66, No. 7, pp. 2445–2446, No. 27052u, Feb. 1967.
Clinical Chemistry, vol. 25, No. 4, pp. 531–534, Apr. 1979.
Beutler et al., Transfusion, vol. 6, No. 6, pp. 537–542 (1966).
Dawson et al., Transfusion, vol. 18, No. 3, pp. 347–352 (1978).
Chemical Abstracts, vol. 89, No. 17, pp. 144, 193, No. 144188c, Oct. 1978.

Primary Examiner—Sidney Marantz
Assistant Examiner—Amalia L. Santiago

[57] ABSTRACT

Inclusion in a blood sample of an isomer of glucose which is capable of replacing glucose in blood cell metabolism ensures accuracy of glucose assay.

8 Claims, No Drawings

PRESERVATION OF GLUCOSE IN BLOOD

This is a continuation of copending application Ser. No. 037357 filed on Mar. 30, 1987; now abandoned.

The invention relates to a method for collecting, transporting or storing of blood using certain additives. These additives should ensure that the glucose level in blood does not fall at all or only to a slight extent in the collected blood.

In conjunction with the collection and storage of blood it has been shown that the glucose content in collected blood continuously falls (Testfibel Glucoquant® glucose, company paper Boehringer, Mannheim, 1984, page 23), so that a loss of more than 10% may occur when the blood is stored at room temperature for about one hour (Thomas, Labor und Diagnose, 2. Edition, Die Medizinische Verlagsgesellschaft, Marburg/Lahn, 1984, page 118). The loss is due to the metabolism of the surviving blood cells, which still consume glucose after the blood sample has been taken. In order to overcome these changes in the composition of blood for purposes of laboratory investigations, suitable substances are added to the blood immediately after taking the blood, which inhibit the metabolism of the blood cells, to prevent the cells from consuming glucose. This method is widely used.

Syringes and storage containers, where the toxic substances are already contained, are commercially available. Preferably, salts of iodoacetic acid (Clinical Chemistry, volume 21 (1975), page 1810; Clinical Chemistry, volume 24 (1978), page 998) and fluorides, for example NaF and KF (Thomas, Labor und Diagnose, 2. Edition, Die Medizinische Verlagsgesellschaft, Marburg/Lahn, 1984, page 119; R. Richterich and J.P. Colombo, Klinische Chemie, 4. Edition, S. Karger, Basel, Munich, Paris, London, New York, Sydney, 1978, page 307; W. Rick, Klinische Chemie und Mikroskopie, 3. Edition, Springer Verlag, Berlin, Heidelberg, New York, 1974, page 177) are used.

However, the use of the mentioned substances reducing the loss of glucose has some disadvantages.

1. Bringing blood in contact with these substances results in damage to blood cells.
2. The consumption of glucose in only insufficiently reduced.

As to 1.: The damage the blood cells receive manifests itself in changes of permeability, among others, so that substances from within the cell go into the plasma. Thus, the concentration of these substances is artificially changed in the plasma, so that the analytical determination shows results which do not represent the true conditions in freshly collected blood. Especially affected are diagnostically very important substances, like potassium and enzymes (Clinical Chemistry, volume 26 (1980), page 1228). Furthermore, the conventionally added substances have an influence on the analytical methods in some cases, so that false test results may also be obtained in this manner. For example, the determination of urea is affected by fluorides (Clinical Chemistry, volume 20 (1974), page 876) and the determination of creatine kinase is affected by iodoacetate (Clinical Chemistry, volume 26, (1980), page 1228). Due to the required relatively high molar concentrations of fluorides, a number of additional changes occur because of osmotic reasons alone. Moreover, in the case of use of fluorides, coagulation of blood will be prevented, so that no choice exists to perform tests in plasma as well as in serum.

The result of these limitations is that a separated blood sample is required exclusively for the analysis of glucose while many other parameters can be analysed from a single sample. This is particularly disadvantageous if modern large testing devices are used. Therefore, in a recently issued description of a multianalytical system (Labormedizin, Heft 1/1985, page 17) the parameter "glucose" is not mentioned.

As to 2.: With the above mentioned compounds the consumption of glucose is only insufficiently reduced. For example, despite the use of fluorides only 88.1–89.9% of the original glucose level can be found 2 hours after the blood has been taken (Clinical Chemistry, volume 28 (1982), page 190). Other authors find 91.9% (The Lancet, 1984, page 1165 and 1985, page 704). Mixtures of fluorides and salts of iodocetic acid also give unsatisfactory results (Clinical Chemistry, volume 25 (1979), page 531).

The present invention involves the use of a principle which up to now has never been used for the problem of preservation of glucose in blood samples. According to this new principle the consumption of glucose is reduced by addition of substances which are chemically similar to glucose. They replace glucose from its active locations in the metabolism of blood cells. Accordingly, glucose is consumed more slowly, or not at all. All substances of the group of the carbohydrates as well as their derivatives which can take the place of glucose in the metabolism of the bood cells may be used. By taking advantage of these possibilities two separate areas of use can be obtained.

1. In contrast to the use of toxic compounds the blood cells are not affected when using the suggested substances. Therefore, the concentrations of other known blood constituents are not falsified through penetrating of substances from damaged blood cells into the plasma. The preservation of glucose in whole blood with the suggested substances makes the analysis of glucose, in addition to other parameters, from a single blood sample, possible for the first time. With the substances proposed in the present invention glucose is conserved at least as well as with the commonly used toxic substances.

2. Neither method, the one using toxic substances nor the one proposed in the present invention is able to prevent completely the consumption of glucose and the reduction of its concentration. As already mentioned, the glucose level in blood falls despite the use of the conventionally preserving agents, for example, to 89 to 92% of the initial values within two hours. However, since the conventional method and the method invented here are based on different mechanisms, improved effects of preservation can be obtained by using both methods simultaneously. After a two hour storage of whole blood in the presence of both types of preserving agents 99% of the original glucose concentration is still available.

Due to certain reasons the glucose in the blood of newborns is even more difficult to preserve than the glucose in the blood of adults. In this case especially remarkable improvements are shown using both methods simultaneously.

For each of the two areas of use only one defined form of application is described out of numerous other possible forms of applications. Accordingly, containers which are suitable for receiving 2 ml whole blood, for example plastic tubes, have to be filled
1. with 4 mg D-mannose,
2. with 4 mg D-mannose and 5 mg potassium fluoride.

The substances can be introduced in an aqueous solution and can subsequently be dried; in this manner, no volume changes of the blood occur due to the added substances.

The commercial utility of the invention is obvious, since containers of blood samples which are filled with the conventional preserving agents for glucose have been available for a long time.

We claim:
1. Method of determining the glucose content of a sample of whole blood collected in a container which comprises including in said container an isomer of glucose capable of replacing glucose in the metabolism of blood cells, and isomer being present in an amount equal to at least 0.1 mg per ml of sample, and
thereafter determining the glucose content of said sample.
2. Method as claimed in claim 1 in which said isomer is d-mannose.
3. Method as claimed in claim 2 in which there is included in said container, in addition to said isomer, a member selected from the group consisting of a fluoride and an iodoacetate.
4. Method as claimed in claim 1 in which there is included in said container, in addition to said isomer, a member selected from the group consisting of a fluoride and an iodoacetate.
5. Method of determining the glucose content of a sample of whole blood which comprises drawing said sample into a container within which is disposed an isomer of glucose capable of replacing glucose in the metabolism of blood cells, said isomer being present in an amount equal to at least 0.1 mg per ml of sample, and
thereafter subjecting said sample to an assay for glucose.
6. Method as claimed in claim 5 in which said isomer is d-mannose.
7. Method as claimed in claim 6 in which there is included in said container, in addition to said isomer, a member selected from the group consisting of a fluoride and an iodoacetate.
8. Method as claimed in claim 5 in which there is included in said container, in addition to said isomer, a member selected from the group consisting of a fluoride and an iodoacetate.

* * * * *

UNITED STATES PATENT AND TRADEMARK OFFICE
CERTIFICATE OF CORRECTION

PATENT NO. : 4,833,090
DATED : May 23, 1989
INVENTOR(S) : Eberhard Liss et al.

It is certified that error appears in the above-identified patent and that said Letters Patent is hereby corrected as shown below:

Title page:

U.S. Patent Documents, "Caborit" is changed to --Laborit--.

Other Publications, "No. 27052u" is changed to --No. 27053u--.

Abstract title should be --Abstract of the Disclosure--.

Column 3, line 18, "and" is changed to --said--.

Signed and Sealed this

Ninth Day of January, 1990

Attest:

JEFFREY M. SAMUELS

Attesting Officer

Acting Commissioner of Patents and Trademarks